(12) United States Patent
Wang et al.

(10) Patent No.: US 6,312,913 B1
(45) Date of Patent: Nov. 6, 2001

(54) METHOD FOR ISOLATING AND CHARACTERIZING NUCLEIC ACID SEQUENCES

(75) Inventors: Jonathan T. Wang, San Francisco; Glenn K. Fu, El Cerrito; Walter H. Lee, Campbell; Laura L. Stuve, Los Gatos, all of CA (US)

(73) Assignee: Incyte Genomics, Inc., Palo Alto, CA (US)

( * ) Notice: Subject to any disclaimer, the term of this patent is extended or adjusted under 35 U.S.C. 154(b) by 0 days.

(21) Appl. No.: 09/620,926

(22) Filed: Jul. 21, 2000

(51) Int. Cl.[7] ............................... C12Q 1/68; C12P 19/34
(52) U.S. Cl. .............................................. 435/6; 435/91.2
(58) Field of Search .................... 435/6, 91.2; 536/24.2, 536/24.33

(56) References Cited

U.S. PATENT DOCUMENTS 5,846,721 * 12/1998 Soares et al. ............................ 435/6

OTHER PUBLICATIONS

Collasius M, Puhta H, Schlenker S and Valet G. Analysis of unknown DNA sequences by polymerase chain reaction (PCR) using a single specific primer and a standardized adaptor. J Virol. Methods, 32: 115–119, 1991.*
Helfman DM, Fiddes JC, Hanahan D. Directional cDNA cloning in plasmid vectors by sequential addition of oligonucleotide linkers. Methods Enzymol., 152: 349–59, 1987.*
Wu R, Wu T, Ray A. Adaptors, linkers, and methylation. Methods Enzymol., 152: 343–349, 1987.*
Sambrook J, Fritsch EF and Maniatis T. Molecular Cloning: A laboratory Manual. 2nd Edition. Cold Spring Harbor Laboratory, Cold Spring Harbor, NY., 13.70–13.72, 1989.*
Kang c, Inouye M. One–step insertion of oligonucleotide linkers or adaptors to DNA using unphosphorylated oligonucleotides. Biotechniques 15(4): 659–62, 665–666, 668, 1993.*
Monday SR, and Bohach GA. Use of Multiplex PCR to detect classical and newly described pyrogenic toxin genes in Staphylococcal Isolates. J clin Microbiol., 37(10): 3411–3414, 1999.*
Beck et al., (1988), "Increased Specificity of PCR–amplified products by size–fractionation of restriction enzyme–digested genomic DNA." *Nucleic Acids Research*, vol. 16(18):9051.

Haqqi et al. (1988), "Specific amplification with PCR of a refractory segment of genomic DNA." *Nucleic Acids Research*, vol. 16(24):11844.
Huang, "Inverse PCR Approach to Cloning cDNA Ends." *Methods in Molecular Biology*, vol. 69:89–96.
Jones et al. (1993), "Genome Walking with 2– to 4–kb Steps using Panhandle PCR." *PCR Methods and Applications*, vol. 2:197–203.
Jones et al. (1992), "Sequence specific generation of a DNA panhandle permits PCR amplification of unknown flanking DNA." *Nucleic Acids Research*, vol. 20(3):595–600.
Lagerstrom et al. (1991), "Capture PCR: Efficient Amplification of DNA Fragments Adjacent to a Known Sequence in Human and YAC DNA." *PCR Methods and Applications*, vol. 1(2):111–119.
Mullis et al. (1986), "Specific Enzymatic Amplification of DNA In Vitro: The Polymerase Chain Reaction." *Cold Spring Harbor Symposia on Quantitative Biology*, vol. 51:263–273.
Ochman et al. (1988), "Genetic applicatiosn of an Inverse Polymerase Chain Reaction." *Genetics*, vol. 120:621–623.
Rudenko et al. (1993), "Supported PCR: an efficient procedure to amplify sequences flanking a known DNA segment." *Plant Molecular Biology*, vol. 21:723–728.
Saiki et al. (1988), "Primer–Directed Enzymatic Amplification of DNA with a Thermostable DNA Polymerase." *Science*, vol. 239:487–491.
Saiki et al. (1985), "Enzymatic Amplification of β–Globin Genomic Sequences and Restriction Site Analysis for Diagnosis of Sickle Cell Anemia." *Science*, vol. 230:1350–1354.
Schaefer (1995), "Revolutions in Rapid Amplification of cDNA Ends: New Strategies for Polymerase Chain Reaction Cloning of Full–Length cDNA Ends." *Analytical Biochemistry*, vol. 227(2):255–273.
Sommer et al. (1989), "Minimal homology requirements for PCR primers." *Nucleic Acids Research*, vol. 17(16):6749.
Wang (2000), "Characterization of Flanking Sequences Using Long Inverse PCR." *BioTechniques*, vol. 28(5):839–843.

* cited by examiner

*Primary Examiner*—Eggerton A. Campbell
*Assistant Examiner*—Prabha Chunduru
(74) *Attorney, Agent, or Firm*—Paula Borden; Bozicevic, Field & Francis, LLP

(57) ABSTRACT

The present invention provides methods for determining nucleic acid sequences based on known sequences adjacent to the unknown sequences, and reagents for using such methods.

22 Claims, 4 Drawing Sheets

Attach Linker

Attach Adaptor

First Amplification

Second Amplification

Isolated Product, *e.g.*, for Characterization

SEQUENCE LISTING

```
<160> NUMBER OF SEQ ID NOS:  3

<210> SEQ ID NO 1
<211> LENGTH: 12
<212> TYPE: DNA
<213> ORGANISM: Artificial Sequence
<220> FEATURE:
<223> OTHER INFORMATION: synthesized primer

<400> SEQUENCE: 1
ctttccagca ca                                                          12

<210> SEQ ID NO 2
<211> LENGTH: 8
<212> TYPE: DNA
<213> ORGANISM: Artificial Sequence
<220> FEATURE:
<223> OTHER INFORMATION: synthesized primer

<400> SEQUENCE: 2 gaaaggtc                                                                8

<210> SEQ ID NO 3
<211> LENGTH: 136
<212> TYPE: DNA
<213> ORGANISM: Artificial Sequence
<220> FEATURE:
<223> OTHER INFORMATION: adaptor

<400> SEQUENCE: 3
ctgggctctt ctatagtgtc acctaaatgc ggccgcgtaa tacgactcac tatagggcga     60
ccagtgtggt gtgacccgag aagatatcac agtggattta cgccggcgca ttatgctgag    120
tgatatcccg ctggtc                                                    136
```

METHOD FOR ISOLATING AND CHARACTERIZING NUCLEIC ACID SEQUENCES

FIELD OF THE INVENTION

The present invention relates to a method for identifying unknown nucleic acid sequences based on known nucleic acid sequences. In particular, the present invention is directed to methods for identifying coding or regulatory regions of a gene based on a known sequence.

BACKGROUND OF THE INVENTION

The polymerase chain reaction (PCR) is a method which permits the specific in vitro amplification of DNA sequences (Mullis et al., *Cold Spring Hath. Syrup. Quant. Biol.,* 51:263–273 (1986); Saiki et al., *Science,* 239:487–491 (1988); Saiki et al., *Science,* 230: 135–1354 (1985). PCR occurs by primer annealing to and extension from a template nucleic acid. Conventionally, PCR is performed using two primers that are complementary to known sequences in the template, each flanking a region of the template nucleic acid that is to be amplified. PCR is used in a wide variety of applications in a wide range of fields from molecular biology to forensics to paternity testing. Regardless of its application, the basis for any of the PCR-based assays is that a region of DNA is amplified billions fold. This makes the process of purifying a target sequence from other sequences unnecessary, as the target sequence will be the overwhelming product of the reaction.

PCR is useful for the cloning of unknown flanking cDNA sequences when part of the cDNA sequence is known. A number of methods such as rapid amplification of cDNA ends (RACE), anchored PCR, and asymmetric PCR have been used to identify flanking regions. These techniques have been used to identify sequences 3' and 5' of the known sequence.

A major obstacle in existing methods for the PCR amplification of specific sequences is the occurrence of nonspecific amplification products. Under PCR conditions, the stringency of the priming (Sommer and Tautz, *Nucleic Acids Res.,* 17:6749 (1989)) is seldom high enough to generate a pure product longer than 1 kilobase (kb) in highly complex mixtures. This limits both the purity of the reaction product and the length of the amplifiable DNA. The use of nested primers (Haqqi et al., *Nucleic Acids Res.,* 16:11844 (1988) and size selection of the regions of interest by gel purification of the template (Ochman et al., *Genetics,* 120:621–623 (1988); Beck and Ho, *Nucleic Acids Res.,* 16:9051 (1988)) diminish this problem, but high background due to insufficient stringency during the PCR amplification of genomic DNA remains a significant problem. Methods to amplify unknown flanking DNA using nested PCR or with gel purified template still result in limited specificity, as the initial PCR amplification using these methods does not improve upon the specificity level conferred by conventional two primer PCR.

Many PCR techniques have been developed for sequencing DNA fragments flanking known sequences. Of them, inverse PCR is a matter of interest because of the simplicity of its principle. (Huang S H., *Methods Mol Biol.*69:89–96 (1997)). However, the protocols for inverse PCR introduced to date use time-consuming procedures, and the methods are limited by the number of suitable restriction enzymes and the presence of restriction sites in the DNA of interest.

Another method that has permitted the highly specific amplification of >2 kb of unknown DNA that flanks a known sequence from bulk human genomic DNA is panhandle PCR (Jones and Winistorfer, Nucleic Acids Res., 20:595–600 (1992); Jones and Winistorfer, *PCR Methods Applic.,* 2:197–203 (1993)). This method involves primer-dependent attachment of a known sequence to the uncharacterized flanking region of a specific DNA strand which contains an unknown sequence. Generation of the panhandle template permits PCR amplification of the unknown DNA because known sequence now flanks the unknown DNA in those strands that contain the unknown DNA. However, in the panhandle PCR method, the initial priming during the amplification reaction must compete with intra-strand annealing of a long inverted repeat that comprises the handle of the panhandle template, which diminishes the efficiency of this necessary first step.

There is thus a need in the art for a method of identifying sequences both 5' and 3' of known sequences, which method provides greater specificity and less contamination products from the genomic sequences.

SUMMARY OF THE INVENTION

The present invention provides methods for isolating polynucleotides flanking a known nucleic acid sequences and reagents for using such methods.

One embodiment of the invention provides a method comprising the steps of 1) attaching a linker to the ends of a nucleic acid which has both known and unknown nucleic acid sequences; 2) attaching an adaptor to the nucleic acid via the linkers to form a circularized nucleic acid; and 3) performing an amplification reaction using the circularized nucleic acid as a template, with one primer specific to the known nucleic acid sequence, and a second primer specific to the adaptor. The reaction is designed to produce a product having unknown sequences of the nucleic acid. The product can then be sequenced to determine the unknown sequences. This method is illustrated in FIG. 1.

Another embodiment of the invention provides a method having the steps of 1) attaching a linker to the ends of a nucleic acid; 2) attaching an adaptor to the nucleic acid via the linker to form a circularized nucleic acid; 3) performing an first amplification reaction using the circularized nucleic acid as a template and two primers specific to the known region of the nucleic acid to obtain a product; and 4) performing a second amplification reaction using the product as a template, with one primer specific to the known nucleic acid sequence, and a second primer specific to the adaptor. The linker preferably provides ends that are compatible for the binding and ligation of the adaptor, but are incompatible for self-ligation of the nucleic acid without the adaptor. The adaptor allows for increased accuracy of the first amplification step, resulting in fewer amplification artifacts and higher efficiency of subsequent amplifications. The second amplification product provides a selection step to identify the products that are specific to the molecules having an adaptor, thus enriching the population of amplification products to increase the number of products that provide the sequence of the nucleic acid flanking the portion having a known sequence. The method is illustrated in FIG. 2.

In another embodiment, the invention provides a method for performing simultaneous amplification reactions on multiple circularized nucleic acids. In this embodiment, the primers used to amplify each circularized nucleic acid are preferably designed to allow maximum efficiency for the amplification reaction of each sample. For example, primers can be designed to have similar $T_m$s, e.g., by determination of G-C content of the primers, and are preferably designed to avoid secondary structure of the primer. The design of the primers can also be automated using a computer program which can identify appropriate primers for use in the present invention.

A feature of the invention is that the first amplification product can be further selected prior to the second amplification reaction.

Another feature of the invention is that additional amplifications may be performed following the second amplification to firther select for a desired final product.

Yet another feature of the invention is that primers to multiple nucleic acids can be designed using an automated selection process, e.g., a computer program.

An advantage of the present invention is that fewer nonspecific products are produced, particularly in the first amplification reaction.

Another advantage of the methods of the invention is that they may be used to isolate and characterize sequences 3' and/or 5' of a known sequence of a nucleic acid.

Yet another advantage of the present invention is that sequences 3' and 5' of the known sequences can be determined using a single circularized template.

Yet another advantage of the invention is that it is useful for high throughput of determination of multiple sequences.

Yet another advantage of the invention is that the method is not limited by a need for restriction sites within the nucleic acid of interest.

These and other objects, advantages, and features of the invention will become apparent to those persons skilled in the art upon reading the details of the methods as more fully described below.

DETAILED DESCRIPTION OF PREFERRED EMBODIMENTS

Figure 1:
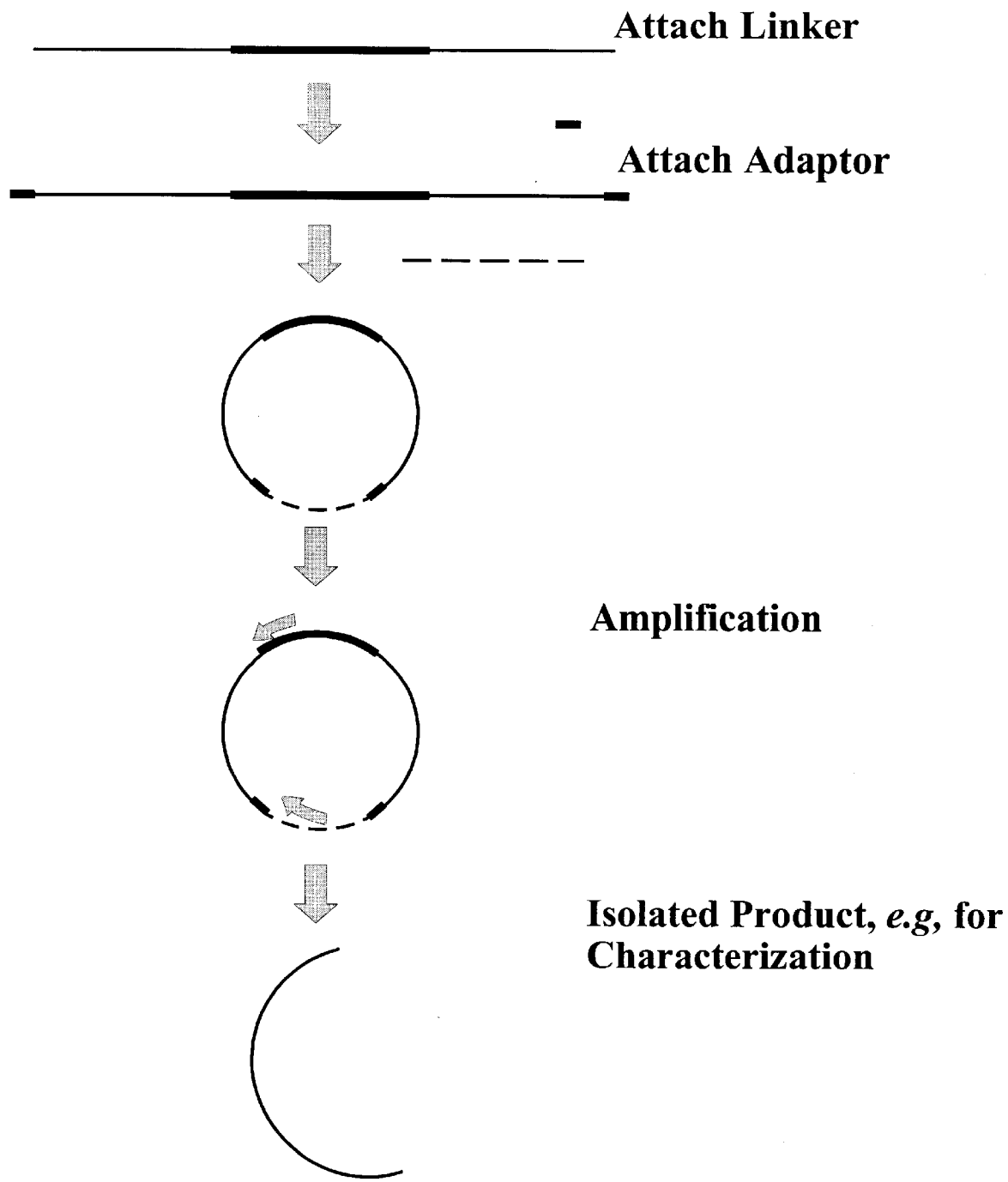
FIG. 1 illustrates a first general embodiment of the invention. The dashed line indicates adaptor, the thin line represents unknown sequences of a nucleic acid, and the bold line represents known sequences of the nucleic acid. Primers are denoted by arrows.

Before the present methods are described, it is to be understood that this invention is not limited to particular conditions and order of methodology described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "and", and "the" include plural referents unless the context clearly dictates otherwise. Thus, for example, reference to "a primer" includes a plurality of such primers and reference to "the nucleic acid" includes reference to one or more copies of a nucleic acid and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Definitions

The term "nucleic acid" as used herein refers to any polynucleotide, and is intended to encompass RNA (including mRNA), and DNA, (including genomic and cDNA). The term is also intended to encompass RNA or DNA having analogs or substitutions to the structure of the nucleic acid, provided the analogs or substitutions do not impede the ability to isolate and/or characterize the sequence of the desired region of the nucleic acid.

The term "linker" as used herein refers to a polynucleotide that is added to an end of a selected nucleic acid to allow subsequent ligation of the adaptor to the nucleic acid. The linker preferably provides sequences flanking the selected nucleic acid that are complementary to the ends of an adaptor, but that will not allow self-ligation of the nucleic acid with the attached linker.

The term "adaptor" as used herein refers to a polynucleotide used to bridge the ends of a nucleic acid to circularize the nucleic acid. The adaptor is generally designed to be complementary to the linker sequences for directional cloning of the adaptor to the nucleic acid. The adaptor may also be directly cloned to the nucleic acid.

The term, "attaching" as used herein, and particularly as it is used with respect to the linker and the adaptor, includes both the covalent or non-covalent, preferably covalent, association of polynucleotides, e.g., a selected nucleic acid and a linker or a linker and an adaptor. For example, attaching may be achieved by hybridization and ligation of the polynucleotides. Attachment may also be achieved using high affinity moieties such as avidin and biotin.

The term "primer" as used herein refers to a polymer of nucleotides capable of acting as a point of initiation of DNA synthesis when annealed to a nucleic acid template under conditions in which synthesis of a primer extension product is initiated, i.e., in the presence of four different nucleotide triphosphates and a polymerase in an appropriate buffer ("buffer" includes pH, ionic strength, cofactors, etc.) and at a suitable temperature. Generally, a primer will be between 12 and 100 nucleotides, more preferably between 15 and 80 nucleotides, and even more preferably between 18 and 50 nucleotides. The primer may be composed of naturally-occurring and/or modified nucleotides, and the modified nucleotides may have a base substitution (e.g., an analog with improved binding), a modified internucleoside linkage, or a substitution of the ribose group.

A primer that hybridizes to a sequence refers to a primer that is complementary to a strand of the nucleic acid and/or a strand of the adaptor. A primer that hybridizes to the coding region of a nucleic acid, or the corresponding strand of the adaptor, will have an "antisense" sequence, i.e., the primer will form Watson-Crick base pairing with the coding region. A primer that hybridizes to a sequence complementary to a sequence will have a "sense" sequence, i.e., it will have the same sequence as the coding region of the nucleic acid or the corresponding strand of the adaptor. For an amplification reaction, generally one primer hybridizes to the sense strand and a second primer hybridizes to a sequence complementary to the sense strand.

The term "hybridization", as used herein refers to the formation of a duplex structure by two single stranded nucleic acids due to complementary base pairing. Hybridization can occur between complementary nucleic acid strands or between nucleic acid strands that contain minor regions of mismatch. Stability of a nucleic acid duplex is measured by the melting temperature, or "$T_m$". The $T_m$ is the temperature (under defined ionic strength and pH) at which 50% of the base pairs have dissociated. Those skilled in the art of nucleic acid technology can determine duplex stability empirically considering a number of variables including, for example, the length of the nucleic acids, base composition and sequence, ionic strength, and incidence of mismatched base pairs.

The term "stringent hybridization conditions" as used herein refers to conditions under which only fully complementary nucleic acid strands will hybridize. Stringent hybridization conditions are well known in the art (see, e.g., Sambrook et al., 1985, Molecular Cloning—A Laboratory Manual, Cold Spring Harbor Laboratory, Cold Spring Harbor, N.Y.) Generally, stringent conditions are selected to be about 5° C. lower than the $T_m$ for the specific sequence at a defined ionic strength and pH. Typically, stringent conditions will be those in which the salt concentration is at least about 0.2 M at pH 7 and the temperature is at least about 60° C. Relaxing the stringency of the hybridizing conditions will allow sequence mismatches to be tolerated; the degree of mismatch tolerated can be controlled by suitable adjustment of the hybridization conditions.

The term "substantially complementary" as used herein refers to two single-stranded nucleic acids that are complementary except for minor regions of mismatch. Stable duplexes of substantially complementary sequences can be achieved under less stringent hybridization conditions. Those skilled in the art of nucleic acid technology can determine duplex stability empirically considering a number of variables including, for example, the length and base pair concentration of the nucleic acids, ionic strength, and incidence of mismatched base pairs.

The term "amplification reaction" as used herein refers to any in vitro means for multiplying the copies of a target sequence of a nucleic acid. Such methods include but are not limited to polymerase chain reaction (PCR).

The term "amplifying" as used herein refers to an exponential increase in a target nucleic acid sequence. The term is used is being used herein to describe both linear and exponential increases in the numbers of a select target sequence of nucleic acid.

The terms "target sequence" and "target nucleic acid sequence" as used herein refer to a region of the nucleic acid which is to be amplified. The target sequence resides between the two primer sequences used for amplification.

General Aspects of the Invention

The invention provides improved methods for determining unknown sequences adjacent to known sequences of a nucleic acid. The methods of the invention provide increased efficiency, particularly of the first amplification step, as the adaptor is designed to be shorter than conventional vector sequences. The product of the first amplification step thus contains fewer sequences that are not specific to the nucleic acid of interest, and the product produced using methods of the invention are generally shorter than the product using techniques such as conventional inverse PCR. Amplification of shorter sequences is more efficient than amplification of longer sequences, as fewer failure products (i.e., incomplete amplification products) are produced when amplifying a shorter nucleic acid fragment. The use of the adaptor in the present methods thus results in a higher percentage of complete products in the first amplification step compared to a similar amplification of the nucleic acid in a conventional vector, e.g., using inverse PCR.

Figure 2:
FIG. 2 illustrates a second general embodiment of the invention. The dashed line indicates adaptor, the thin line represents unknown sequences of a nucleic acid, and the bold line represents known sequences of the nucleic acid. Primers are denoted by arrows.
Figure 2:
Figure 2:
Figure 2:

Two embodiments of the invention are illustrated in FIGS. 1 and 2. In these exemplary embodiments, a linear nucleic acid is provided for determining sequences flanking the known sequences of the nucleic acid, which are shown in bold. First, a linker molecule is added to the ends of the nucleic acid. The linker molecule is preferably a short polymer of nucleotides that is complementary to the ends of the adaptor, but which are not self-complementary, i.e., the nucleic acid with linkers will not self-circularize. The linker is incubated with and ligated to the nucleic acid to attach a linker to each end of the nucleic acid.

Following attachment of the linker to the nucleic acid, an adaptor with ends complementary to the linkers is attached by incubation and ligation of the adaptor with the nucleic acid. The addition of the adaptor results in the formation of a circularized nucleic acid, which can be used directly or purified prior to use in the subsequent amplification steps.

In a first embodiment, the circularized nucleic acid is used as a template in an amplification with one primer that hybridizes to a known nucleic acid sequence and a second primer that hybridizes to an adaptor sequence. This product can be directly used to determine the unknown sequences of the nucleic acid. See FIG. 1. The product of this amplification reaction can be further selected by using the product as a template with the same primers or with nested primers specific to the nucleic acid and the adaptor, or the product may be cloned into a vector prior to sequence determination.

In a second embodiment, illustrated in FIG. 2 the circularized nucleic acid template is used in an amplification reaction with two nucleic acid-specific primers to produce a first amplification reaction product. This product will include any nucleic acid sequences 5' and 3' of the known sequences. The product of the first amplification reaction mixture can be used directly as template for the second amplification, or the first amplification reaction mixture can be diluted.

The second amplification uses the product of the first amplification as the template with one primer that hybridizes to a known nucleic acid sequence and one primer that hybridizes to the adaptor. The primers can be chosen to amplify the unknown sequences either 3' to the known sequences (as shown) or 5' of the known sequences, depending on the selected directionality of the primer pair. Thus, the present methods can be used to isolate and/or characterize the sequence of a nucleic acid 3' of the known sequences, 5' of the known sequences, or both.

Figure 3:
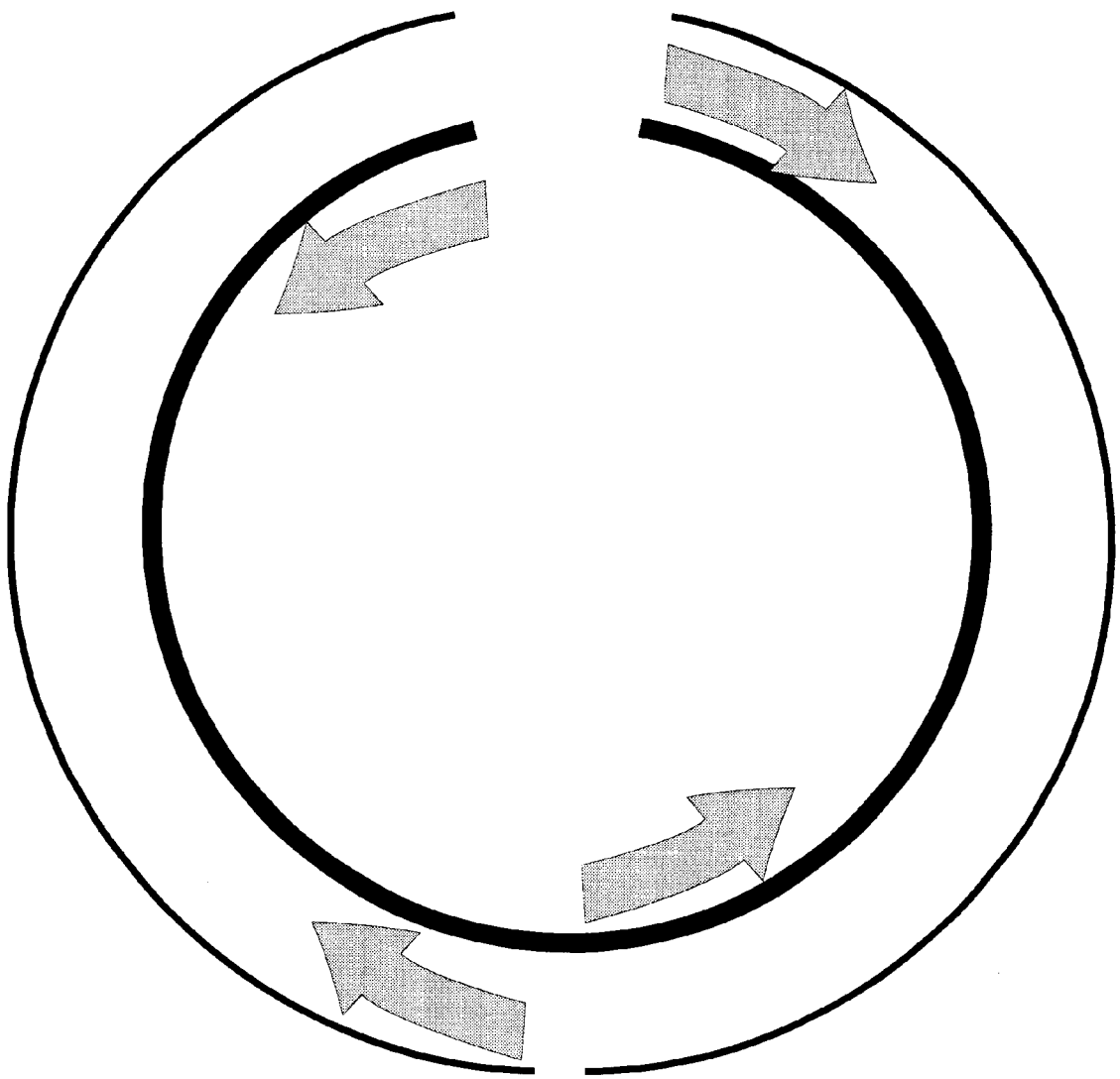
FIG. 3 illustrates another embodiment of the invention illustrating determination of both 3' and 5' unknown sequences. The thick line represents a first amplification product, and the thin lines represent isolated product from an additional amplification using the first amplification product as a template. Primers are denoted by arrows.

To isolate unknown sequences both 3' and 5' of the known nucleic acid sequences, the first amplification product can be used as a template for two separate second amplification reactions, the first reaction using a primer that hybridizes to the sense strand of the nucleic acid and a primer that hybridizes to sequences complementary to the adaptor, and the second reaction using a primer that hybridizes to sequences complementary to the nucleic acid and a primer that hybridizes to the sense strand of the adaptor. This embodiment is illustrated in FIG. 3.

In another embodiment of the invention, the first amplification product is further selected prior to the second amplification reaction. The product may be selected by numerous techniques including size selection (e.g., gel purification) and additional amplification using nested primers specific to the nucleic acid.

In another embodiment of the method, additional amplifications may be performed following the second amplification to further select the final product, e.g., the product of the second amplification can be used as a template for additional amplification using nested primers, one specific to the nucleic and one specific to the adaptor. This is illustrated in FIG. 3.

In yet another embodiment, the entire method may be carried out simultaneously for multiple nucleic acids as a high-throughput method to provide information about multiple nucleic acids. Following circularization of the different nucleic acids, multiple separate amplification reactions can be performed simultaneously to determine unknown sequences of the multiple known nucleic acid regions. Primers for each of the reactions can be designed to have similar or identical $T_m$s upon annealing to the target nucleic acid, and are preferably designed to avoid secondary structure of the primer. The design of the primers can also be automated using a computer program which can identify appropriate primers for use in the present invention.

The length of the unknown sequence of a nucleic acid, the position of previously designed primers within the known sequence of the nucleic acid, the desired length of the primer, the base content of the primer, and other criteria can be used to determine the search regions for the design of primers either manually or using a program. For example, a program can be given a predetermined search start and stop position for a forward primer depending on the length of the nucleic acid to be amplified and the location of a corresponding reverse primer. Preferably, the region to be amplified is 300 nucleotides or less, although primers can be designed to amplify larger nucleic acid regions. Typically, the primers are also designed to be as close to the unknown region as possible to maximize the amount of information obtained on the unknown sequence.

The instruments used to perform the amplification reactions are preferably controlled by computers which are user-programmable, such as a personal computer (PC) or an internal microprocessor based controller of conventional design, adapted to receive data defining the desired protocols and to carry out the protocol by issuing the proper control signals to operate the necessary equipment.

For example, the methods of the invention can be controlled by a processor that will control the construction of the template nucleic acids and/or the temperature and time of each step in the amplification reaction cycles. The processor executes system control software, which is a computer-readable program stored on a computer-readable medium available for access by the processor, e.g., stored in a memory coupled to processor. Memory may be a hard disk drive or may be other kinds of portable memory, such as a floppy disk, a zip disk or a CD-rom. The system can include a hard disk drive, a floppy disk drive and/or a card rack. The processor can operate under the control of the system control software, which includes sets of instructions that dictate the parameters of a particular process, including the addition of certain reagents, time, temperature, etc. Other computer programs such as those stored on other memory including, for example, a floppy disk or other computer program product inserted in a disk drive or other appropriate drive, may also be used to operate the processor.

Adaptor Design

The adaptor can be designed to be of a length and G-C content that will bind to at least one primer sequence under stringent hybridization conditions. The adaptor is preferably shorter than conventional vector sequences, thus maximizing the amount of target nucleic acid sequence generated in the first amplification reaction. Although the adaptor can be up to 2–3 kb in length, the adaptor is preferably between 15 nucleotides to 1 kb in length, more preferably is between 20 and 500 nucleotides in length, even more preferably 30–250 nucleotides in length, and even more preferably 50–100 nucleotides in length. The ends of an adaptor of the invention are generally designed to be complementary to the ends of the linker used for a nucleic acid. The adaptor may be composed of naturally-occurring and/or modified nucleotides, and the modified nucleotides may have a base substitution, a modified internucleoside linkage, or a substitution of the ribose group.

When it is desirable to perform nested amplification reaction using a primer to the adaptor, at least a portion of the adaptor sequences must be known sequences to allow for primer design. If nested amplification reactions are not desirable, the sequence of the adaptor need not be known as long as the ends of the adaptor are compatible for hybridization with the linkers.

Although the invention is primarily described herein as having a linking group between the nucleic acid and the adaptor, the present invention is also intended to encompass an adaptor designed to directly hybridize to the nucleic acid. For example, determination of the sequence of a genomic DNA fragment can use DNA having different overhanging sequences, e.g., from digestion of the genomic region with two separate restriction endonucleases. In such a case, the adaptor may be designed to have ends complementary to the digested nucleic acid, and the adaptor can be added to the nucleic acid directly.

Primer Design

The choice of primers for use in amplification reactions determines the specificity of the amplification reaction. Primers used in the present invention are polymers comprised of nucleotides, and preferably deoxyribonucleotides, that can be extended in a template-specific manner by the amplification reaction.

The primer sequence need not reflect the exact sequence of template nucleic acid. For example, a non-complementary nucleotide fragment (e.g., a site for a restriction endonuclease) may be attached to the 5' end of the primer with the remainder of the primer sequence being complementary to the template. In addition, non-complementary bases can be interspersed into the primer, provided that the primer sequence has sufficiently complementary for annealing and synthesis of a complementary DNA strand.

The primers are designed to be sufficiently long to prime the synthesis of extension products in the presence of the agent for polymerization. Short primer molecules generally require cooler temperatures to form sufficiently stable hybrid complexes with the template. The primers of the invention are preferably designed to bind to either a nucleic acid sequence or an adaptor sequence with high affinity, preferably forming stable Watson-Crick base pairing at 55–65° C. The primers specific to the adaptor can be designed to have a desired $T_m$ upon annealing and little or no predicted secondary structure. $T_m$ can be determined based on G-C content, length of the primer, and the like. Similarly, primers specific to the nucleic acid can be complementary to a selected region of the nucleic acid with particular G-C content, predicted secondary structure, and $T_m$. In addition, stretches of a particular base (and specifically A's or T's) can be taken into account and avoided in the primer design. Preferably, primer pairs that will be used in a single amplification reaction are designed to have the same or similar $T_m$ upon annealing to the template. Other techniques for determining primer advantageous primer characteristics can be found in *PCR Applications: Protocols for Functional Genomics*, Ed. Michael A. Innis, Academic Press (May 1999) and *PCR: Essential Techniques* Ed. J. F. Burke, John Wiley & Son Ltd (December, 1996), which is incorporated herein by reference.

The primers to nucleic acid sequences may be designed manually, or, for highthroughput experiments, can be designed using an automated system such as a computer program. Such a program can be used to determine an area of a nucleic acid that has the desired characteristics (e.g., G-C content, $T_m$, etc.). Thus, if amplification reactions are to be run with multiple nucleic acid samples, the primers can be designed to all have the same or similar characteristics with respect to stringency to maximize the efficiency of the reaction for each nucleic acid sample.

The primers may also be designed to have restriction endonuclease sites in the primer to allow cloning of the amplification products into vectors for sequencing. The restriction sites are preferably at or near the 5' end of the primer so that it does not affect the binding of the primer or extension of the amplification product. The primer may have additional nucleotides 5' to the restriction site to increase efficiency of cleavage by the restriction endonuclease.

Amplification Reactions

Numerous amplification techniques known in the art can be used in the present invention including PCR. PCR amplification of a nucleic acid involves repeated cycles of heat-denaturing the nucleic acid, annealing two primers to sequences that flank the nucleic acid to be amplified, and extending the annealed primers with an appropriate polymerase. The primers hybridize to opposite strands of the target sequence and are oriented so that synthesis by the polymerase proceeds across the region between the primers, effectively doubling the amount of the segment. Moreover, because the extension products are also complementary to and capable of binding primers, each successive cycle essentially doubles the amount of nucleic acid synthesized in the previous cycle. This results in the exponential accumulation of the specific target fragment, at a rate of approximately $2^n$ per cycle, where n is the number of cycles.

For the amplification of DNA, a thermostable polymerase such as *Thermus aquaticus* (Taq) DNA polymerase or pfu polymerase can be used. Methods for the preparation of Taq are disclosed in U.S. Pat. No. 4,889,818 and incorporated herein by reference. Methods for the preparation of pfu polymerase are disclosed in U.S. Pat. No. 4,889,818 and incorporated herein by reference. Other thermostable DNA polymerases isolated from other Thermus species (e.g., *Thermus thermophilus* or *Thermotoga maritima*) or non-Thermus species, as well as non-thermostable DNA polymerase such as T4 DNA polymerase, T7 DNA polymerase, *E. coli* DNA polymerase I, or the Klenow fragment of *E. coli*, can also be used in the PCR of DNA.

The present invention can be used to isolate and/or characterize sequences adjacent or directly flanking any nucleic acid having a known sequence. For example, the present invention may be used to determine the 5' and/or 3' ends of a cDNA by using a cDNA as a template in the first amplification reaction. The linker is thus added to cDNA, either purified preparation of a single cDNA or in a pool of such molecules (e.g., an the cDNA products of a reverse transcription reaction or inserts from a cDNA library). In a case where the unknown sequences are from a genomic DNA region, the genomic region is preferably digested prior to the first reaction with an enzyme that is not predicted to cut the genomic region in the area of interest. The genomic DNA can be further selected (e.g., size selected using gel purification or chromatography) prior to attaching the linker to the DNA to better purify the template and to increase efficiency of the first amplification reaction.

Alternatively, the RNA itself may be circularized with the adaptor and linker, and the reverse transcription and/or amplification process performed on the circularized RNA. If a circularized RNA is used as the template of the amplification reactions, the enzyme is a thermostable enzyme capable of amplifying RNA using primer extension. The enzyme can be an RNA polymerase that produced DNA from RNA, e.g., a reverse transcriptase such as MMLV-RT or ALV-RT. Methods for reverse transcribing RNA into cDNA are well known and described in Maniatis et al., supra. This enzyme could be used for a first reaction, and then the remaining amplification reactions would take place as described for DNA, i.e., the first cycle would be reverse transcription, and the remaining cycles would be conventional PCR. For example, U.S. Pat. No. 5,322,770 describes a procedure for coupled reverse transcription/amplification of an RNA template using a thermostable DNA polymerase. In another example, U.S. Pat. No. 5,916,779 describes a process in which cDNA copies of an RNA target sequence are generated and amplified concurrently.

Those skilled in the art will recognize that whatever the nature of the nucleic acid, the nucleic acid can be amplified merely by making appropriate and well recognized modifications to the method being used.

A variety of techniques for extracting nucleic acids from biological samples are known in the art. For example, see those described in Maniatis et al., Molecular Cloning: A Laboratory Manual (New York, Cold Spring Harbor Laboratory, 1982); Arrand, Preparation of Nucleic Acid Probes, in pp. 18–30, Nucleic Acid Hybridization: A Practical Approach (Ed Hames and Higgins, IRL Press, 1985); or, in PCR Protocols, Chapters 18–20 (Innis et al., ed., Academic Press, 1990).

In certain protocols, the addition of reagent such as dNTPs, enzyme or primers may be desired during the amplification reaction protocol (e.g., in the later cycles), or continuous addition of reagents may be desired. Additions of reagents during the amplification process can be done manually or, more preferably, additions can be done automatically under the control of CPU via a reagent addition mechanism. For example, a CPU can be coupled to a cycle counter via a control mechanism where the number of cycles completed are monitored during the protocol. Reagent additions later in the protocol can maximize the total yield. For example, fidelity can be improved by keeping the dNTP concentrations in the 10–50 micromolar range, but these levels might prove to be stoichiometrically limiting in later cycles. Therefore, an increase in Mg-dNTP concentration late in the amplification protocol may improve yield dramatically with little net effect on accuracy. Similarly, primer concentration may be increased in late cycles to boost total yield and/or to provide increased product purity.

Figure 4:
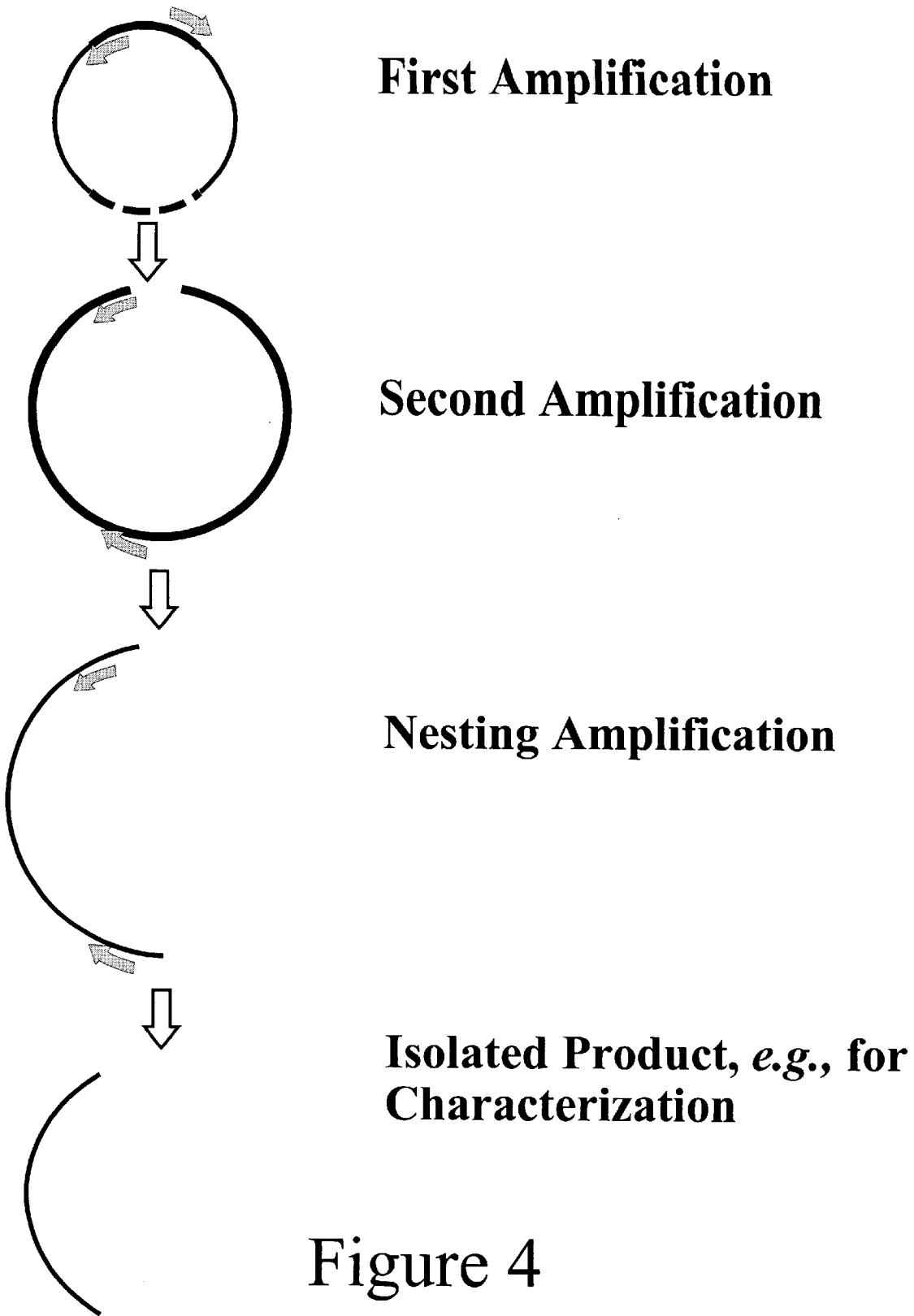
FIG. 4 illustrates a nesting amplification reaction for further selection of DNA containing the unknown sequences. The dashed line indicates adaptor, the thin line represents unknown sequences of a nucleic acid, and the bold line represents known sequences of the nucleic acid. Primers are denoted by arrows.

Nested primers can be used to ensure the specificity of the amplification products. For example U.S. Pat. No. 4,683,195 demonstrates the use of nested primers to decrease the background in the amplification of single copy genes. This procedure requires a first primer pair to amplify a target sequence and a second primer pair to produce a product using the first target sequence as a template. Following either the first or second amplification reaction, the reaction mixture is diluted to reduce the concentration of the first primer pair, and the second primer pair is introduced into the reaction mixture. Alternatively, the reaction product can be isolated following amplification, and the purified product used as template for the FIG. 4 illustrates a nested amplification reaction following the second amplification reaction. Other modified nesting amplification procedures can also be used. Examples of such reactions are described in U.S. Pat. No. 5,994,056.

Additional Amplification Reagents

The nucleoside-5'-tiphosphates utilized in the extension process, typically dATP, dCTP, dGTP, and dTTP, are present in total concentration typically ranging from 400 $\mu$M to 4.0 mM during the extension reaction, although preferably the concentration is between 500 $\mu$M and 1.5 mM. Amplification systems such as PCR also require a buffer compatible with the enzymes used to amplify the target nucleic acid sequence.

The pH of an amplification mixture affects the stability of the template nucleic acid. Increasing the pH of the reaction can decrease the degradation of template nucleic acid during thermal cycling. Although PCR amplification mixtures are pH buffered, the pH of a typical PCR reaction varies considerably during the temperature cycling because of the temperature dependence of the reaction buffer. The buffering agent used in a typical PCR is Tris, which has a $\Delta$pKa of −0.031 per ° C. The fluctuation in pH during the temperature cycling can be decreased by using a buffering agent with a smaller $\Delta$pKa, such as Tris(hydroxymethyl)methylglycine (tricine), which has a $\Delta$pKa of −0.021 per ° C., and N,N-Bis(hydroxyethyl)glycine (bicine), which has a $\Delta$pKa of −0.018 per ° C. (both values measured at 20° C.), and 0.1M ionic strength (see Good and Izawa, 1972, Meth. Enzymol. 24, Part B:53–68). With either a tricine or bicine buffer, the pH remains higher during the high temperature reaction conditions than with the typical Tris buffer, and the fluctuations in pH caused from the temperature cycling are decreased.

Both monovalent and divalent cations can be used in the amplification reactions. The preferred divalent cation for the amplification of DNA is $Mg^{2+}$. A number of monovalent salts can also be used in the methods of the present invention, including but not limited to KCl, KOAc NaCl, $(NH_4)_2$, $SO_4$, K-glutamate, and $NH_4OAc$. The optimum level of each of these can be determined empirically by one skilled in the art to provide adequate stringency and/or yield.

Analysis of the Amplification Product

Following the final amplification, the product for analysis may be used directly to determine the sequence of the product, purified (e.g., gel purification or precipitation), or cloned into a conventional vector. Suitable vectors include plasmid vectors having a bacterial origin site for replication in competent bacterial cells, and restriction sites for cloning into the vector. Exemplary vectors include pBluescript (Stratagene, La Jolla, Calif.), pVP16 (Clontech, Palo Alto, Calif.), and the pcDNA series of vectors (Invitrogen, Carlsbad, Calif).

Sequencing may be carried out using any techniques known by those skilled in the art, including but not limited to Maxam-Gilbert sequencing, Sanger sequencing, and, more preferably, fluorescent sequencing. In a preferred embodiment, the sequencing is performed using fluorescent dye sequencing on a capillary sequencer, e.g., a Molecular Dynamic Megabase capillary sequencer (Pharmacia Upjohn, Peapack, N.J.). These systems are typically controlled by programmable computers such as a PC or an internal microprocessor based controller of conventional design.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g., amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Example 1

A method of the invention was performed with 21 known GenBank genes, and the method directly compared with standard RACE protocols using either the Clontech Marathon kit or the Ambion RLM-RACE kit. The methods for these RACE protocols were carried out according to manufacturer's protocols, and both RACE kits were used for each gene. If both kits resulted in a clone, the longer of the two protocols was used to achieve a longer extension. The protocols were performed for the following genes:

| | KNOWN GENE | Genbank ID | Genbank ID description | Size of protein (aa) | Transcript Length |
|---|---|---|---|---|---|
| 1 | Ion Channel | g4101566 | Two-pore potassium channel TPKCl [Homo sapiens] | 426 | 2106 |
| 2 | Secreted Enzyme | g180950 | Carboxyesterase [Homo sapiens] | 566 | 1966 |
| 3 | Protease | g5689463 | KIAA 1063 protein [Homo sapiens] | 593 | 5223 |
| 4 | Phosphatase, tyr | g35794 | Protein-tyrosine phosphatase [Homo sapiens] | 610 | 1884 |
| 5 | adme-sulfo | g3769610 | ATP sulfurylase/APS kinase 2 [Homo sapiens] | 614 | 2014 |
| 6 | Protease | g179644 | Human complement C1r [Homo sapiens] | 705 | 2493 |
| 7 | GPCR | G3366802 | Orphan G protein-coupled receptor HG38 | 907 | 2880 |
| 8 | Protease | g5923788 | Zinc metalloprotease ADAMTS7 [Homo sapiens] | 997 | 3179 |
| 9 | Phospholipase | g3811347 | Cytosolic phospholipase A2 beta [Homo sapiens] | 1012 | 3352 |
| 10 | Protease | g6693824 | Ubiquitin-specific protease [Homo sapiens] | 1055 | 3803 |
| 11 | Protease-aspartic | g5802824 | Gag-Pro-Pol protein [Homo sapiens] | 1117 | 9422 |
| 12 | Ion Channel | g6715117 | MTR1 [Homo sapiens] | 1165 | 3912 |
| 13 | Kinase | g1805500 | ASK1 [Homo sapiens] | 1375 | 4525 |
| 14 | GPCR [Homo sapiens] | g4034486 | Latrophilin-2 [Homo sapiens] | 1403 | 4669 |
| 15 | ABC Transporter | g1574998 | Canalicular multispecific organic anion transporter [Homo sapiens] | 1545 | 5300 |
| 16 | ABC Transporters (p-glycoprotein) | g4240130 | KIAA0822 protein [Homo sapiens] | 1581 | 5677 |
| 17 | Protease cathepsin | g179665 | Complement component C3 [Homo sapiens] | 1663 | 4678 |
| 18 | Ion Channel | g5689485 | KIAA1074 protein [Homo sapiens] | 1709 | 5360 |
| 19 | Protease | g5802821 | Gag-Pro-Pol protein [Homo sapiens] | 1879 | 9486 |
| 20 | Protease | g5802814 | Gag-Pro-Pol-Env protein [Homo sapiens] | 2294 | 9181 |
| 21 | NHR | g2358287 | ALR [Homo sapiens] | 4957 | 14874 |

A method of one embodiment of the invention was also performed for the same 21 genes. cDNA was obtained via random priming of an mRNA preparation and ligated into either pcDNA2.1 or an adapter of the invention. First strand synthesis was performed in a 20 μRT reaction with 10 ng pDN6 random primer and ~1 μg mRNA per reaction. The mRNA was incubated at 25° C. for 5 min, and then 1 μl of MMLV-RNaseH-Reverse Transcriptase (Superscript II, Gibco, Rockville, Md.) was added and the temperature was raised to 42° C. and the mRNA was incubated an additional 45 min. 1 μl of Thermoscript polymerase was added, and the reaction was subjected to subsequent incubations of 50° C. for 10 min, 55° C. for 30 min, and 60° C. for 10 min. These steps were to ensure the longest possible cDNA conversion.

Following incubation, the following reagents were added to the reaction: 91 μl dH2O, 3 μl dNTP, 1 μl *E. coli* ligase, 4 μl Pol I, and 1 μl RNase H. The reaction was incubated at 16° C. 2 hrs. 2 μl T4 pol was added to the reaction, and the reaction was incubated for an additional 5 min at 16° C. Following this second incubation, 10 μl of EDTA was added to stop the reaction. The reaction was phenol-chloroform extracted and the cDNA EtOH precipitated.

The reaction was ligated to a BstXI linker (Invitrogen, Carlsbad, Calif.) and incubated at 16° C. overnight. The linker used had the sequence 5' CTTTCCAGCACA (SEQ ID NO:1) and 3' GAAAGGTC (SEQ ID NO:2). Following incubation, the cDNA was purified using a Chromospin 1000 (Clontech, Palo Alto, Calif.). Following purification, a portion of the reaction was ligated to an adapter of the invention to form circular template for the first amplification step. All of the cDNA generated was ligated to an adaptor sequence at an estimated 1:1 molar ratio of cDNA:adaptor, to minimize the formation of template concantamers. The adaptor used was an oligonucleotide with the sequence 5'pCTGGGCTCTTCTATAGTGTCAC-CTAAATGCGGCCGCGTAATACGACTC ACTAT-AGGGCGACCAGTGTGGTGTGAC-CCGAGAAGATATCACAGTGGATTTACGCCG GCGCATTATGCTGAGTGATATCCCGCTGGTCp 5' (SEQ ID NO:3).

The first amplification reaction was performed on the circularized DNA products of each of the genes in a 96 well plate in a final reaction volume of 20 μl. Each 20 μl reaction well contained the following: 15.9 μl dH₂O; 2 μl 10× buffer (50 mM Tris-HCl pH 9.1, 16 mM ammonium sulfate, 3.5 mM MgCl₂ and 150 mg/ml BSA); 1 μl 10 mM dNTP; 1 μl Template (0.5 ng/μl); and 0.1 μl (25 u/μl); KlenTaq/pfu mix (KlenTaq=25 u/μl, pfu=2.5 u/μl; 150:1 u/u:Ktaq/pfu mix) (KlenTaq was from Ab Peptides, St. Louis, Mo.; pf polymerase was from Stratagene, La. Jolla, Calif.). Primer and water mix was added by 12 channel pipetting, and the reactions took place using a Perkin Elmer thermocycler. The cycling conditions were: 95° C. for 30 sec, 57° C. for 30 sec, and 68° C. for 12 min (or 10 min for GMC adapter ligated template) for 40 cycles total.

The product of the first amplification reaction was then diluted to a final volume of 100 μl in TE pH 8.0 and HPLC water (1:2).

The second amplification reaction was performed in a 96 well plate in a final reaction volume of 30 μl. Each well contained the following: 25.35 μl 1× long PCR mix; 0.5 μl template (diluted product from the first reaction); 1 μl forward primer (complementary to the adaptor); 1 μl reverse primer (complementary to nucleic acid); 2 μl HPLC grade water; and 0.15 μl Klentaq/pfu. Primer and water mix was added by 12 channel pipetting, and the reactions took place using a Perkin Elmer thermocycler. The cycling conditions were as follows: 95° C. for 1 min; 95° C. for 30 sec; 57° C. for 30 sec; and 68° C. for 5 min for 40 cycles total with a final extension of 20 min at 68° C.

Following the second amplification step, the products were gel purified and cloned for sequencing. 20 μl PCR product was added to 2 μl 10× loading dye and loaded onto a 1.4% low-melt gel with thin combs. The gels were run slowly for good separation. A number of samples were purified using Gelase/β-agarase followed by EtOH precipitation. Other samples were purified using a Qiagen gel extraction kit followed by EtOH precipitation. The pellets were resuspended in a small volume of dH$_2$O (5–10 μl).

The samples were each cloned and transformed into chemically competent cells using 2–4 μl of sample. This process was repeated for samples where a smaller number of clones were obtained. Cells were plated onto Kanamycin plates and cells with inserts were identified using blue/white selection. 12 colonies were picked for each sample, and the inserts sequenced.

The following results were obtained for the methods of the invention and the standard RACE protocols:

|  | Method of Invention | Standard RACE |
|---|---|---|
| Number of full-length genes isolated | 8 | 2 |
| Average extension length (for all transcripts) | 966 bps | 267 bps |
| Average extension for transcripts > 3kb | 1005 bps | 138 bps |
| Number of genes specifically extended (specificity) | 18 | 14 |

Thus, the present invention isolated a larger number of full-length genes, had a better efficiency of extension in the first amplification, and identified a higher number of genes than did the conventional RACE protocol. The method of the invention also has a particular advantage in extending long transcripts, i.e. transcripts over 3 kb, with an average extension 7 times that of standard RACE protocols.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

That which is claimed is:

1. A method for isolating sequences of a nucleic acid, comprising the steps of:
   attaching a first linker to a 3' end of the nucleic acid and a second linker to a 5' end of the nucleic acid, said nucleic acid comprising known sequences and unknown sequences;
   attaching an adaptor to the ends of the nucleic acid via the linkers to form a circularized nucleic acid; and
   performing an amplification reaction to produce an amplification product comprising the adaptor and unknown sequences.

2. The method of claim 1, wherein the amplification reaction comprises:
   the circularized nucleic acid;
   a primer that hybridizes to a known nucleic acid sequence; and
   a primer that hybridizes to a sequence complementary to the adaptor.

3. The method of claim 1, wherein the amplification reaction comprises:
   the circularized nucleic acid;
   a primer that hybridizes to a sequence complementary to a known sequence; and
   a primer that hybridizes to an adaptor sequence.

4. A method for isolating sequences of a nucleic acid, comprising the steps of:
   attaching a first linker to a 3' end of the nucleic acid and a second linker to a 5' end of the nucleic acid, said nucleic acid comprising known sequences and unknown sequences;
   attaching an adaptor to the ends of the nucleic acid via the linkers to form a circularized nucleic acid;
   performing a first amplification reaction to produce a first amplification product comprising the adaptor and unknown sequences;
   performing a second amplification reaction using the first amplification product as a template to produce a second amplification product comprising the adaptor and unknown sequences; and
   determining the sequence of the second amplification product.

5. The method of claim 4, wherein the first amplification reaction comprises:
   the circularized nucleic acid; and
   a primer that hybridizes to a known nucleic acid sequence; and
   a primer that hybridizes to a sequence complementary to a known nucleic acid sequence.

6. The method of claim 4, wherein the second amplification reaction further comprises:
   a primer that hybridizes to a known sequence; and
   a primer that hybridizes to a sequence complementary to an adaptor sequence.

7. The method of claim 4, wherein the second amplification reaction further comprises:
   a primer that hybridizes to a sequence complementary to a known nucleic acid sequence; and
   primer that hybridizes to an adaptor sequence.

8. The method of claim 4, wherein each of the amplification steps are polymerase chain reaction amplifications.

9. The method of claim 4 wherein the product of the first amplification is purified prior to the second amplification.

10. The method of claim 4, wherein the product of the first amplification is further selected prior to the second amplification.

11. The method of claim 10, wherein the selection comprises an additional amplification using the primers of the first amplification.

12. The method of claim 11, wherein the selection comprises an additional amplification using at least one primer different from the primers of the first amplification.

13. The method of claim 4, wherein the second amplification product is purified prior to determining the sequences.

14. The method of claim 4, wherein the primers of the second amplification comprise a restriction endonuclease cleavage site, and further wherein the second amplification product is cloned into a vector prior to determining the sequence.

15. The method of claim 1, wherein the adaptor is a polymer comprised of 15 to 1000 nucleotides.

16. The method of claim 15, wherein the adaptor is a polymer comprised of 30–100 nucleotides.

17. The method of claim 16, wherein the nucleic acid is selected fro the group consisting of mRNA, cDNA and genomic DNA.

18. The method of claim 17, wherein the nucleic acid is cDNA, the method further comprising the steps of:
    preparing mRNA from a sample; and
    reverse transcribing the mRNA to produce cDNA.

19. A high-throughput method for determining sequences of multiple nucleic acids based on known sequence of the nucleic acids, comprising the steps of:
    attaching a first linker to a 3' end and a second linker to a 5' end of a plurality of nucleic acids, each nucleic acid comprising known sequences and unknown sequences;
    attaching an adaptor to each nucleic acid via the linkers to form a circularized nucleic acid for each nucleic acid;
    performing a first amplification reaction on each circularized nucleic acid, each reaction comprising:
    a) a circularized nucleic acid,
    b) two primers that hybridize to the known sequences of the circularized nucleic acid, wherein each amplification results in a first product comprising the adaptor; and
    performing a second amplification reaction on each product, each reaction comprising the product of the first amplification, one primer specific to the known nucleic acid sequence, and a second primer specific to the adaptor; and
    sequencing the second amplification product.

20. The method of claim 19, wherein each nucleic acid comprises mRNA and wherein the method further comprises the step of preparing mRNA from a sample.

21. The method of claim 19, wherein each nucleic acid comprises cDNA, and wherein the method further comprises the steps of:
    preparing mRNA from a sample; and
    reverse transcribing the mRNA to produce cDNA.

22. A computer-readable medium having a computer-readable program embodied therein for directing operation of a method for determining sequences of a nucleic acid, the method comprising the steps of:
    attaching a first linker to a 3' end of the nucleic acid and a second linker to a 5' end of the nucleic acid, said nucleic acid comprising known sequences and unknown sequences;

attaching an adaptor to the ends of the nucleic acid via the linkers to form a circularized nucleic acid;

performing a first amplification reaction to produce a first amplification product comprising the adaptor and unknown sequences;

performing a second amplification reaction to produce a second amplification product comprising the adaptor and unknown sequences; said reaction comprising the first amplification product as a template; and determining the sequence of the second amplification product.

\* \* \* \* \*